United States Patent [19]

Muckerheide

[11] Patent Number: 5,191,411

[45] Date of Patent: Mar. 2, 1993

[54] LASER DRIVEN OPTICAL COMMUNICATION APPARATUS

[75] Inventor: Myron C. Muckerheide, Port Washington, Wis.

[73] Assignee: Seton Health Care Foundation, Milwaukee, Wis.

[21] Appl. No.: 467,897

[22] Filed: Jan. 22, 1990

Related U.S. Application Data

[63] Continuation-in-part of Ser. No. 156,732, Feb. 18, 1988, abandoned.

[51] Int. Cl.[5] .......................... H04N 7/18; H04N 5/66; H04N 9/31
[52] U.S. Cl. ...................................... 358/93; 358/230; 358/61
[58] Field of Search ................... 358/93, 94, 230, 231, 358/61; 340/706, 707; 178/18

[56] References Cited

U.S. PATENT DOCUMENTS

| | | | |
|---|---|---|---|
| 4,189,743 | 2/1980 | Schure et al. | 340/707 |
| 4,280,135 | 7/1981 | Schlossberg | 358/93 |
| 4,371,893 | 2/1983 | Rabeisen | 340/707 |
| 4,430,526 | 2/1984 | Brown et al. | 340/707 |
| 4,846,694 | 7/1989 | Erhardt | 340/707 |

*Primary Examiner*—John K. Peng
*Attorney, Agent, or Firm*—Dick and Harris

[57] ABSTRACT

A laser driven optical communication apparatus for permitting verbally impaired or disabled individuals having limited physical mobility to communicate with others. A laser device generating a coherent beam of light is provided wherein the individual directs the beam of light upon an interface screen towards forming images understandable by others. The interface screen serves to cause the beam of light to be reflected and made visible. An optical receiver comprising a modified video camera directed toward the interface screen receives the reflected image and serves to enhance the persistence of the image to cause the beam of light directed by the individual to appear as a single continuous image upon an associated display. A video cassette recorder may be incorporated to permit the images to be stored and replayed at a later time. The present invention may also be used to permit a speaker to "draw" images upon a display being projected upon a display screen such as in a conference hall setting.

16 Claims, 1 Drawing Sheet

LASER DRIVEN OPTICAL COMMUNICATION APPARATUS

This is a Continuation-in-Part of Co-pending application Ser. No. 07/156,732 filed Feb. 18, 1988 now abandoned.

BACKGROUND OF THE INVENTION

The present invention relates generally to communication devices, and, in particular, to a laser driven optical communication apparatus for permitting verbally impaired or disabled individuals having limited physical mobility to communicate with others. The concepts of the present invention may also be used to replace a pointer otherwise used to draw attention to portions of an image projected on a display screen by permitting continuous laser drawn images to persist in superimposition upon the projected display.

Over the years a number of prior art apparata have attempted to address the hardship verbally disabled individuals endure in communicating with others, particularly where the verbally disabled individual suffers from physical immobility which precludes the use of paper and pen to communicate. One prior art communication device comprises an adjustable head pointer consisting of an aluminum wand which is removably attached to an individual's head through the use of head and chin straps such that an individual by moving one's head may point to objects and, for example, may sequentially point to letters of the alphabet printed upon a chart spelling out words towards communicating with others. Another prior art device incorporates a light pointer worn upon an individual's head, or placed at the end of a headstick or wand, wherein movement of the head would direct the light to illuminate the object desired or, potentially, select letters which in combination spelled words towards communicating with others. Unfortunately, however, many of such prior art communication devices have experienced drawbacks which restrict their use to individuals who possess considerable ability to move their head or limbs. Moreover the weight of such prior devices and the need for wide degrees of movement often preclude use of such prior art devices. In addition, the ability to form words and sentences to communicate may be cumbersome due to the need to point to each individual letter appearing on a chart with a wand or light pointer. In particular, conventional prior art light pointers utilize incandescent lamps which produce a broad beam of light thus necessitating that printed indicia be spaced widely apart in order to permit the accurate selection of the desired indicia.

Pointer devices have further been utilized by speakers addressing groups of individuals in conference hall or auditorium settings. One particular prior art device comprises a handheld laser light generator which may be used to draw attention to a particular aspect of a display projected upon an auditorium screen. It is noted however that such a laser pointer generates a particularly focused beam of light which appears merely as a dot upon the screen. As the laser pointer is moved, the projected dot moves in a corresponding motion thus limiting the speaker's use of the prior art device to the relatively simple function of pointing to a single position at any one time.

Accordingly, it is an object of the present invention to provide a laser driven optical communication apparatus which incorporates a laser for producing a coherent beam of light which may be used by individuals having very limited degrees of movement of the head or limbs to communicate with others.

It is additionally an object of the present invention to provide a laser driven optical communication apparatus which permits a nonverbal individual with limited physical mobility to communicate with others by "writing" with a beam of laser light.

It is a further object of the present invention to provide such a laser driven optical communication apparatus which incorporates a video cassette recorder for recording the individual's communications towards simultaneous or future viewing.

It is yet another object of the present invention to provide such a laser driven optical communication apparatus which permits verbally impaired individuals having limited physical mobility to operate a device utilizing a keyboard input apparatus having incorporated therein laser sensors.

Another object of the present invention is to permit several individuals to communicate with each other on the same screen.

It is an additional object of the present invention to permit speakers to generate substantially continuous images superimposed upon images projected upon a display screen.

These and other objects of the invention will become apparent in light of the present specifications and drawings.

SUMMARY OF THE INVENTION

The present invention comprises a laser driven optical communication apparatus for permitting verbally impaired or verbally disabled individuals who have limited physical mobility to communicate with others. The present invention has significant application in an emergency room setting where stroke victims who often arrive with only minimal physical mobility may nevertheless communicate with a doctor to provide lifesaving information. The principles of the present invention may also be used in a conference hall environment wherein laser drawn continuous images or drawings may be superimposed upon other images projected on a large screen.

The present laser driven optical communication apparatus provides a laser means for generating a coherent beam of light wherein the beam of light generated by the laser means may be directed by an individual having even the slightest physical mobility in a manner so as to form images which are understandable by others. These images may comprise alpha-numeric characters which may be combined to form words, or, alternatively, may take the form of more primitive symbolic indicia which nevertheless permit physically and verbally disabled individuals to communicate with others.

An interface screen is provided and is positioned as a target upon which the individual directs the beam of light towards forming the images sought to be communicated. The interface screen serves to cause a portion of the beam of light generated by the laser and directed on the interface screen to be reflected therefrom and made momentarily visible thereon. Accordingly, the individual "writing" with the laser beam generator may follow the path of the beam of light and view same as it is directed across the interface screen to facilitate the formation of the images "drawn" thereon.

An optical receiver means associated with the interface screen means is provided for receiving the portion of the beam of light which is reflected off of the interface screen means. The optical receiving device comprises a conventional closed circuit television camera. Contained within such a typical camera is a device known as a vidicon which comprises an evacuated glass tube with an optically flat targetplate at one end to receive an image. The camera is aimed at the scene so that the optical image is focused on the light sensitive targetplate in the vidicon. An electron beam generated within the vidicon is directed upon and scans the targetplate which beam is in turn converted into a video signal as a function of the scene appearing upon the targetplate.

As is known to those skilled in the art, included within the camera are provisions to control parameters relating to the beam current and target voltage. Adjustment to the potentiometers controlling the beam current potentiometer and target voltage serve to balance the camera's sensitivity with image lag. By adjusting these camera controls image lag can be emphasized such that bright moving objects in the picture appear with a trail extending away from the direction of movement. The camera as adjusted thus serves to enhance the persistence of the reflected beam of laser light to, in turn, cause that beam of light to appear as a single continuous image.

Display means electrically connected to the optical receiver means serve to display the continuous image thereby enabling the directed beam of light to be read by others towards permitting the individual to communicate.

In the preferred embodiment of the invention, the laser means preferably comprises a Class 2 or lower helium-neon (HeNe) laser. Such a laser, preferably emitting at 632.8 nm (though not necessarily limited thereto) generates a visible beam of light which may be used safely in most every application due to its minimal wattage. The preferred embodiment of the invention preferably includes an interface screen which comprises a substantially planar element having a phosphorous-fluorescent material deposited thereon. The phosphorous-fluorescent material serves to render the screen element semi-reflective to both prevent total reflection of the beam of light back at the user's eyes and enhance the persistence of the beam of light reflected from the interface screen means. The optical receiver means preferably comprises a television camera, such as a PANASONIC CCTV Model WV-1410, which is directed toward the interface screen for viewing the beam of light reflected by the screen means as the laser means is moved across in the formation of images thereon. The camera, as adapted, thus records and enhances the persistence of the image.

The display means preferably comprises a cathode ray tube which is electrically connected to the television camera and which serves to permit the viewing of the image thereon. In another embodiment of the invention, the optical communication apparatus further includes a polarization element operably attached to the lens of the camera for further enhancing the persistence of the beam of light reflected from the interface screen means. The use of a polarization element permits the apparatus to be utilized without the necessity of lowering the ambient room light which may otherwise be required due to the increased sensitivity of the camera's vidicon.

In a further embodiment of the invention, the interface screen may take the form of a CRT monitor having a video cassette recorder connected thereto whereby the individual may direct the laser light directly upon the CRT monitor and specifically toward any of the images displayed on the monitor as generated by the video cassette recorder. The optical receiver means is thus directed upon the CRT monitor whereby the optical receiver captures the combination of the images generated by both the cassette recorder and the individual in a manner which captures the individual's "laser written" image as a continuous display.

In an alternative embodiment of the invention, the interface screen means comprises a substantially planar sheet of material which is dyed with a fluorescent material, such as OXAZINE 720 Perchlorate supplied by EXCITON. The dye should preferably be sensitive to the particular laser used, for example, a 632 excitation solution which may be sprayed on the interface surface with an acrylic based coating. The dying, or doping, of the screen serves to modify the reflective quality of the interface screen means to thereby modify the persistence of the reflected beam of light and reduces reflective laser light. Use of a green helium-neon laser in combination with a dyed interface screen causes the beam of light to take on a yellow color after reflection to which the camera has greater sensitivity.

In one embodiment of the invention, attachment means are provided for attaching the laser means to a portion of the individual's body which possesses an ability to engage in at least minimal movement. Accordingly, the individual may direct the beam of light generated by the laser means by moving that portion of his or her body having the laser means attached thereto.

In a further embodiment of the invention, the attachment means comprises eyeglass frames, having the laser means with a self-contained power supply attached, which may be worn upon the individual's head whereby the slightest movement of the individual's head will direct the beam of light in the formation of images upon the interface screen means. Additionally, the attachment means may alternatively comprise a helmet or headband configuration wearable upon the individual's head similarly having the laser means with self-contained power supply attached thereto. The preceding embodiment of the invention would permit an individual who retains even the most limited movement of his head to communicate with others notwithstanding any paralysis of the arms or legs.

The present invention may be used with a fiber optic means having a first end and a second end where the first end is operably attached to the laser means. The fiber optic means is provided capable of directing the coherent beam of light from the laser means to the second end of the fiber optic means. Preferably, the second end of the fiber optic means is attached to that portion of the individual's body which retains at least minimal movement, for example a forefinger, which movement would permit the individual to move the second end of the fiber optic means to direct the beam of light emanating therefrom towards the formation of images to communicate with others. The fiber optic could similarly be affixed to a pair of eyeglass frames for delivery to the interface screen towards formation of images.

In one embodiment of the invention, the apparatus may further include a recording means such as a video cassette recorder, electrically connected to the optical receiver means for electronically storing the images created by the individual toward the simultaneous or future viewing of same.

In an alternative embodiment of the invention, the laser driven optical communication apparatus can permit verbally impaired or disabled individuals having limited physical mobility to operate devices incorporating a keyboard input apparatus. The laser means provided generates a coherent beam of light which may be directed by an individual onto one of a plurality of indicia means having associated therewith laser sensor means. The individual may then direct the beam of light upon the particular laser sensor means associated with a corresponding indicia means to thereby select that indicia means. The laser sensor means can thus produce an output signal upon being illuminated by the beam of light wherein the output signal is electrically connectable to a desired device towards permitting the individual to operate that device.

In yet another embodiment of the invention, a laser driven optical communication apparatus is provided for permitting an individual to supplement or otherwise make "notes" upon an image being projected upon a large conference hall screen. Such apparatus permits the individual to draw or otherwise cause images to be superimposed over an existing image being projected upon a display screen thereby replacing a conventional pointer stick or laser pointer device. An image source such as a video tape cassette player serves to generate the image to be projected, be it static or in motion. The image source is electrically connected to a first projection device such as a projection television. The first projection device serves to project an image upon a display screen, such as in a large conference hall. A laser means is provided for generating a coherent beam of light which may be directed by the individual upon the display screen to "draw" or "write" upon the projected image. The display screen causes a portion of the beam of light to be reflected and which is received by an optical receiver means, such as the above-described modified television camera. The camera serves to enhance the persistence of the reflected beam of light to, in turn, cause the beam of light to appear as a single continuous image. The camera is electrically connected to a second projection device the display of which is projected upon and aligned with the image projected by the first projection device. The laser generated image and the projected image are thereby simultaneously displayed upon the display screen. A video cassette recorder may be connected to the camera to permit storage and delayed viewing of the combined images.

DETAILED DESCRIPTION OF THE DRAWINGS

Figure 1:
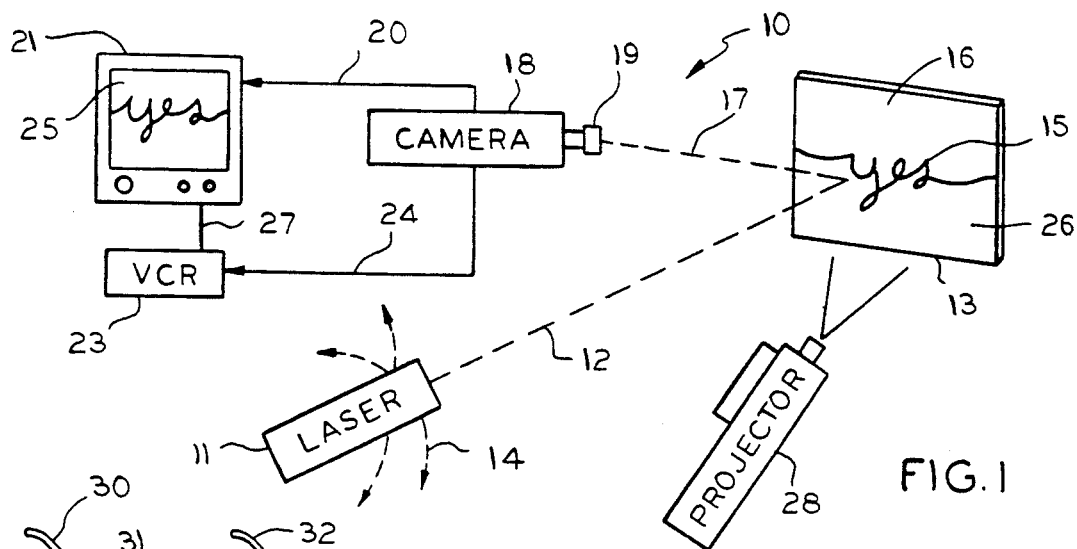
FIG. 1 of the drawings is a schematic representation of the present laser driven optical communication apparatus illustrating the laser means being directed upon the interface means towards forming an image received by the optical receiver means and shown upon the display means and further illustrating the use of a projector means for directing an image upon the interface means.

While this invention is susceptible to embodiment in many different forms, there is shown in the drawings and will herein be described in detail, several specific embodiments, with the understanding that the present disclosure is to be considered as an exemplification of the principles of the invention and is not intended to limit the invention to the embodiment illustrated.

Laser driven optical communication apparatus 10 is shown in schematic representation in FIG. 1. Laser means 11 is shown generating a coherent beam of light 12 which is directed upon interface screen means 13 upon which may be formed images understandable by others. The individual (not shown) may cause the laser means 11 to move as designated by arrows 14 to thus form an image 15 understandable by others. Interface screen means 13 is shown comprising a substantially planar sheet of material upon which is deposited a phosphorous-fluorescent material 26 which serves to render interface means 13 partially reflective. Camera 18 is shown directed toward interface screen means 13 wherein the beam of light 12 generated by laser means 11 is reflected off of the surface 16 of interface means 13 as a beam of light, designated 17. Camera 18 thus views the image 15 which is traced out upon interface screen means 13 by movement of laser means 11.

In present illustration of FIG. 1, the image of the letters "yes" are shown as having been "written" out upon interface screen means 13. In the present invention, long dwell times are not necessary and must be balanced with the erasure times to prevent overlapping images. Typically, interface screen means 13 will not possess a significant degree of persistence such that the beam of light 12 will appear to an ordinary observer as a mere dot upon the surface 16 of interface screen means 13 as the beam of light 12 is traced across screen 13. The momentary illumination of the beam 12 as a dot upon the surface of interface screen means 13 serves to aid the individual in aiming laser means 11 towards facilitating the formation of images. Camera 18, a conventional closed circuit television camera, modified as described herein, serves to provide the required persistence of the image traced out upon interface screen means 13 such that a complete continuous image (in this example the letters "y", "e" and "s" forming the word "yes") appears on display means 21.

Display means 21 is shown comprising a standard television set having screen 25. Camera 18 is shown attached by cable 20 to display means 21. In addition, video cassette recorder 23 is shown connected to camera 18 by cable 24 whereby the images which appear upon screen 25 of display means 21 may be recorded for simultaneous or future viewing by connection to display means 21 through cable 27. For example, through such an arrangement, "electronic letters" could be written by a verbally impaired individual and sent to and played at a remote location or indexed to a printer to provide hardcopy printout as well as permitting the generation of a legal signature in hard copy. FIG. 1 of the drawing further illustrates polarizing means 19 operably attached to the lens of camera 18. Polarizing means 19 serves to further enhance the persistence of the image 15 formed upon the surface 16 of interface screen means 13 by the beam of light 12 and overcome the camera's sensitivity to ambient light.

Projector 28 is further shown projecting an image upon interface screen 13 which image, together with image 15 is captured by camera 18. In operation, projector 28 could project a background image comprising for example multiple choice questions or graphic images such as outlines of a human body whereby the individual could "answer" the projected questions or make reference to particular parts of the body to thus communicate to emergency room personnel.

It is contemplated that projector 28 could comprise any image generating device such as a slide projector, or the like.

Figure 2:
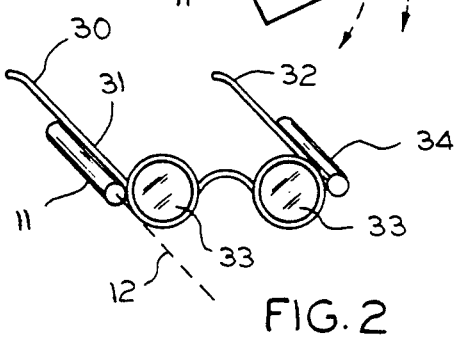
FIG. 2 of the drawings is a side perspective view of the embodiment of the present invention incorporating the laser means affixed to attachment means which are shown comprising eyeglass frames containing lenses.

FIG. 2 of the drawings illustrates a conventional pair of eyeglasses. Laser means 11 is shown operably affixed to the right earpiece 31 of eyeglass frames 30. Power supply 34 is shown operably attached to the left temple 32 of eyeglass frames 30 which supplies power to laser means 11 towards the generation of the beam of light 12. Lenses 33 are similarly shown.

In operation, the individual need only wear eyeglass frames 30 whereby the beam of light 12 generated by laser means 11 will be directed in accordance with the movements of the individual's head wherein the individual's vision serves to accurately aim and target beam of light 12 toward the formation of indicia upon interface screen 13.

Figure 3:
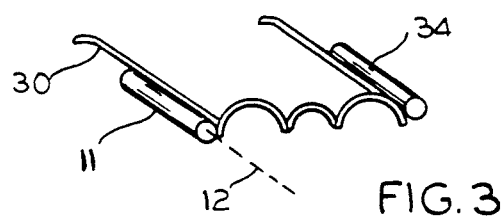
FIG. 3 of the drawings is a side perspective view of the embodiment of the invention illustrating the attachment means of FIG. 2 without lenses.

FIG. 3 of the drawings illustrates another embodiment of the eyeglass frame arrangement of FIG. 2. In this illustration, corrective lenses 33 are omitted and eyeglass frames 30 are shown as comprising half frames only.

Figure 4:
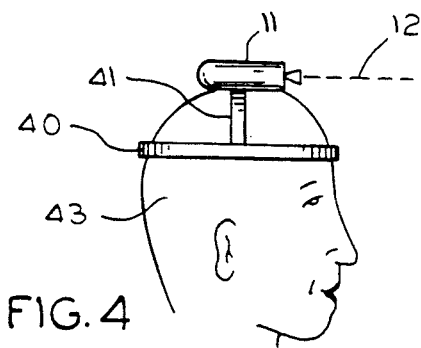
FIG. 4 of the drawings is a side view of the laser means shown affixed to headband means positioned upon the individual's head.

FIG. 4 of the drawings illustrates the attachment of laser means 11 (including a self-contained power supply) to headband means 40 and 41. Headband means 40 and 41 are worn upon the head 43 of the individual whereby the beam of light 12 generated by laser means 11 may be directed by even the slightest movement of the individual's head 43. As is well understood, a few degrees of movement is all that is required to produce a sufficiently large image so long as laser means 11 and the operating individual are positioned a sufficient distance from interface screen means 13.

Figure 5:
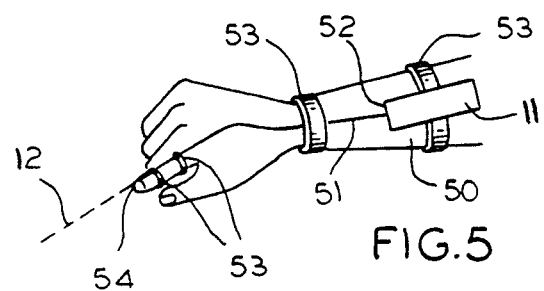
FIG. 5 of the drawings is a side perspective view of the laser means with fiber optic means attached thereto.

FIG. 5 illustrates another embodiment of the invention wherein laser means 11 is shown removably affixed to the individual's arm 50. Fiber optic means 51 is shown having a first end 52 and a second end 54 wherein the first end 52 is shown operably connected to laser means 11. Fiber optic means 51 is further shown removably affixed to the individual's arm 50 by strap means 53 and to the individual's forefinger by strap means 53 such that the second end 54 establishes the point of origin of the beam of light 12 produced by laser means 11. In such an embodiment, only the slightest degree of movement of the forefinger of the individual is required in order to direct the beam of light 12 towards the formation of indicia. In operation, the individual by moving the forefinger directs the beam of light as desired. Alternatively, the fiber optic means could be used to write upon an interface screen means 13. The fiber optic means 51 could alternatively be affixed to eyeglass frames to permit control of the beam of light by movement of the head.

Figure 6:
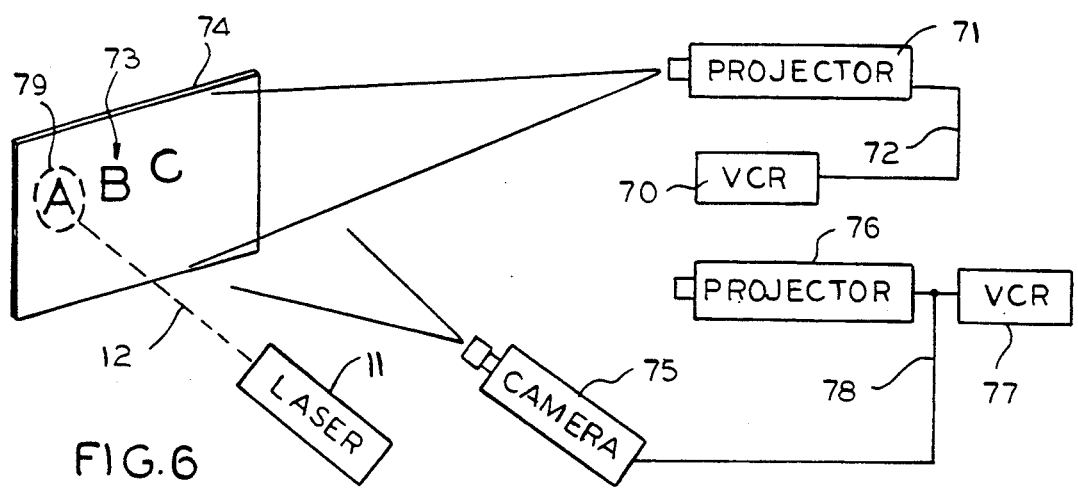
FIG. 6 of the drawings is a schematic representation of another embodiment of present laser driven optical communication apparatus showing the simultaneous display of laser generated images and projected images upon a display screen.

FIG. 6 of the drawings illustrates another embodiment of the present invention which permits an individual to cause written matter to be superimposed upon an image being projected upon a display screen such as would be of use in a conference hall environment. Image source means 70, a video cassette recorder, is shown electrically connected to first projection means 71 by cable 72. First projection means 71 serves to project an image 73 upon a display screen means 74. In the example illustrated, the projected image 73 consists of the letters "A", "B" and "C". Laser means 11 is shown generating a coherent beam of light 12 which is directed upon display screen means 74. The individual (not shown) may use the laser means to direct the beam of light to "write" upon the display screen to supplement the projected image 73 displayed thereon or to otherwise draw additional images upon the projected display. In the example shown, the laser means 11 is shown having drawn a circle 79 around the letter "A" projected by the first projection means 71. While the beam of laser light appearing upon the display screen is of short persistence, camera 75 serves to enhance the persistence and cause a continuous image to appear.

Camera 75 is shown directed upon display screen means 74. Camera 75 which is shown electrically connected to a second projection means 76 by cable 78 which camera 75 serves to receive the beam of light 12 reflected off of display screen 74. The second projection means 76 is directed upon and aligned with the image projected by the first projection means 71 and serves to cause the simultaneous display upon display screen means 74 of the projected images generated by the image source means 70 and the continuous image created by the laser means 11. Video cassette recorder 77 is shown electrically connected to camera 75 by cable 78 so that the combined images projected upon display screen means 74 may be stored for future viewing.

The foregoing description and drawings merely explain and illustrate the invention and the invention is not limited thereto, except insofar as the amended claims are so limited as those skilled in the art who have the disclosure before them will be able to make modifications and variations therein without departing from the scope of the invention.

What is claimed is:

1. A laser driven optical communication apparatus for permitting verbally impaired or disabled individuals having limited physical mobility to communicate with others, said laser driven optical communication apparatus comprising:

laser means for generating a coherent beam of light where-in said beam of light may be directed by said individual in a manner so as to form images understandable by others;

interface screen means positioned as a target upon which said individual directs said beam of light towards the formation of said images, said interface screen means serving to cause a portion of said beam of light directed thereon to be reflected and made visible thereby permitting said individual to follow the path of said beam of light towards facilitating the formation of said images;

optical receiver means associated with said interface means for receiving said reflected portion of said beam of light, said optical receiver means being capable of enhancing the persistence of said reflected beam of light to, in turn, cause said beam of light to appear as a single continuous image;

display means electrically connected to said optical receiver means for displaying said continuous image thus enabling said directed beam of light to be read and permitting said individual to communicate with others.

2. The laser driven optical communication apparatus according to claim 1 in which said laser means comprises a class 2 HENE laser.

3. The laser driven optical communication apparatus according to claim 1 in which said interface screen means comprises a substantially planar element having a phosphorus-fluorescent material deposited thereto so as to render said screen element semi-reflective.

4. The laser driven optical communication apparatus according to claim in which said interface screen comprises a substantially planar dyed sheet which serves to modify the reflective quality of said interface screen means to thereby modify the persistence of said reflected beam of light.

5. The laser driven optical communication apparatus according to claim 1 in which said optical receiver means comprises a television camera wherein the target voltage and beam current are adjusted to a level where light persistence is achieved and increased.

6. The laser driven optical communication apparatus according to claim 1 in which said display means comprises a cathode ray tube display.

7. The laser driven optical communication apparatus according to claim 1 in which the invention further includes an image source means for projecting images upon said interface screen means.

8. The laser driven optical communication apparatus according to claim 1 in which the invention further includes an attachment means for attaching said laser means to a portion of said individual's body which possesses an ability to engage in at least minimal movement whereby said individual may direct said beam of light generated by said laser means by moving said portion of said individual's body.

9. The invention according to claim 8 in which said attachment means comprises eyeglass frames worn upon said individual's head whereby the slightest movement of said individual's head will direct said beam of light towards the formation of images upon said interface screen means.

10. The invention according to claim 8 in which said attachment means comprises a headpiece wearable upon said individual's head.

11. The laser driven optical communication apparatus according to claim 1 in which the invention further includes a polarization element operably attached to said camera means for enhancing the persistence of said reflected beam of light.

12. The laser driven optical communication apparatus according to claim 1 in which the invention further includes a fiber optic means having a first end and a second end, said first end being operably attached to said laser means, said fiber optic means being capable of directing said coherent beam from said laser means to the said second end of said fiber optic means to further enable said individual to direct said beam of light generated by said laser means.

13. The laser driven optical communication apparatus according to claim 1 in which the invention further includes a recording means electrically connected to said optical receiver means for electronically storing said images toward their later viewing.

14. A laser driven optical communication apparatus for permitting an individual to supplement an image being projected upon a large conference hall screen with additional laser generated images, said laser driven optical communication apparatus comprising:

image source means for generating said image to be projected;

projection means operably and electrically connected to said image source means for projecting said image;

display screen means upon which said image projected by said projection means may be viewed;

laser means for generating a coherent beam of light wherein said beam of light may be directed by said individual upon said display screen means and said image being projected thereon and wherein a portion of said beam of light is reflected by said display screen means;

optical receiver means for receiving said reflected beam of light, said optical receiver means capable of enhancing the persistence of said reflected beam of light to, in turn, cause said beam of light to appear as a single continuous image;

second projection means operably and electrically connected to said optical receiver means for simultaneously displaying said continuous image in an aligned manner upon said display screen.

15. The laser driven optical communication apparatus according to claim 14 in which the invention further includes a polarization element operably attached to said optical receiver means for enhancing the persistence of said reflected beam of light.

16. The laser driven optical communication apparatus according to claim 14 in which the invention further includes a video cassette recorder electrically connected to said optical receiver means to permit the storage and delayed viewing of said displayed images.

* * * * *

UNITED STATES PATENT AND TRADEMARK OFFICE
CERTIFICATE OF CORRECTION

PATENT NO. : 5,191,411
DATED : March 2, 1993
INVENTOR(S) : Myron C. Muckerheide

It is certified that error appears in the above-identified patent and that said Letters Patent is hereby corrected as shown below:

Col. 9, Line 22, "according to claim in" should read --according to claim 1 in--.

Signed and Sealed this

Fifteenth Day of March, 1994

Attest:

BRUCE LEHMAN

Attesting Officer     Commissioner of Patents and Trademarks